United States Patent [19]

Weinreb et al.

[11] Patent Number: 5,012,496
[45] Date of Patent: Apr. 30, 1991

[54] DROP COUNTING SYSTEM

[75] Inventors: Robert N. Weinreb, Rancho Santa Fe; Jerzy J. Lewak, Del Mar; Andreas W. Dreher, San Diego, all of Calif.

[73] Assignee: Acumetric, Inc., San Diego, Calif.

[21] Appl. No.: 433,014

[22] Filed: Nov. 7, 1989

[51] Int. Cl.⁵ ............................................. A61M 5/172
[52] U.S. Cl. ..................................... 377/21; 604/246; 604/253; 222/420; 222/422; 377/6
[58] Field of Search ................. 377/21, 6; 222/21, 57, 222/58, 420, 422

[56] References Cited

U.S. PATENT DOCUMENTS

| | | | |
|---|---|---|---|
| 4,037,598 | 7/1977 | Georgi | 222/14 |
| 4,321,461 | 3/1982 | Walter et al. | 377/21 |
| 4,372,150 | 2/1983 | Stephens et al. | 377/21 |
| 4,397,642 | 8/1983 | Lamadrid | 222/14 |
| 4,469,480 | 9/1984 | Figler et al. | 222/14 |
| 4,635,281 | 1/1987 | Jones | 377/21 |
| 4,934,564 | 6/1990 | Piatt | 222/420 |

Primary Examiner—John S. Heyman
Attorney, Agent, or Firm—Spensley Horn Jubas & Lubitz

[57] ABSTRACT

An electronic apparatus for counting and recording a number of drops of fluid. The preferred embodiment of the invention is configured as a molded receptacle housing for receiving a commercially available eyedrop bottle in which the cap has been replaced by the housing. The invention includes a detection means that detects the separation of drops from a fluid supply bottle, and counts and records the number of such drops in a preset time period. Optionally, a real-time clock time stamps the stream of drop count data so that the absolute time period during which drops are released is also ascertained and recorded. Optionally, a reminder signal or indication is given to a patient as to the dosage and appropriate time for each eyedrop administration, or an alarm is given if over or under medication is occurring. An alternative application is disclosed in which the drop detection and counting features of the invention are used in a feedback loop to control the flow of fluid in a drop metering system.

26 Claims, 8 Drawing Sheets

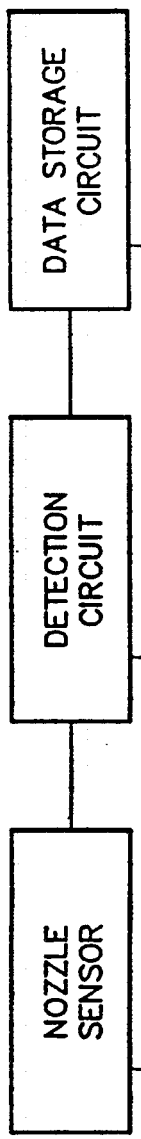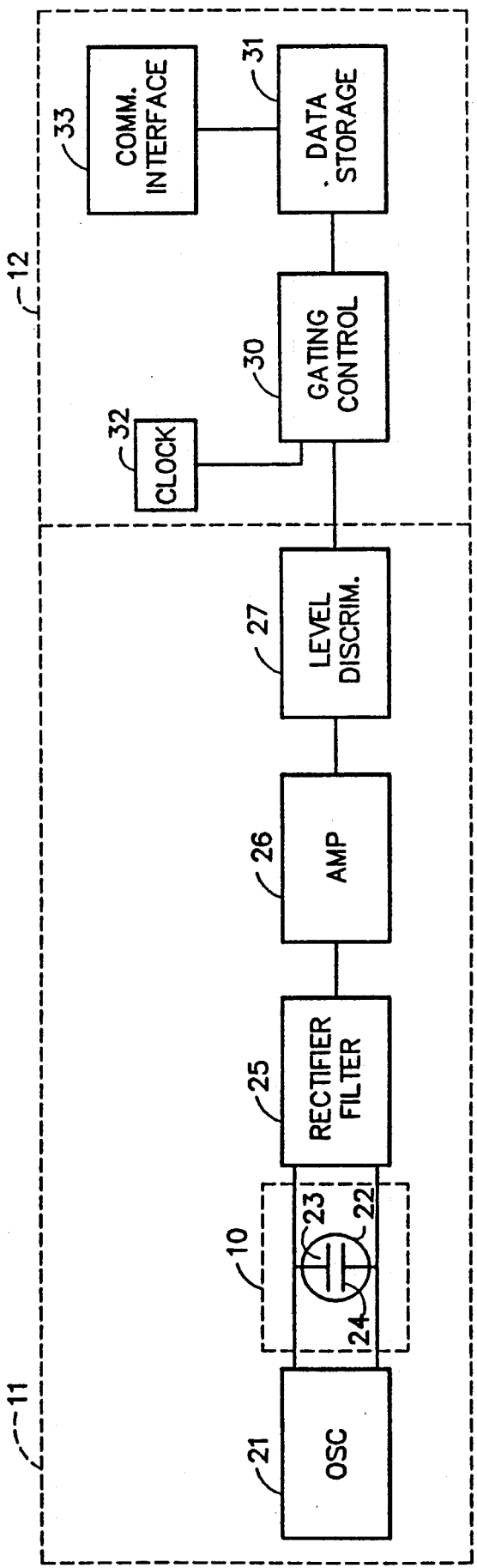

DROP COUNTING SYSTEM

BACKGROUND OF THE INVENTION

1. Field of the Invention

This invention relates to electronic counting and recording devices, and more particularly to an electronic apparatus for counting and recording a number of drops of fluid.

2. Description of Related Art

In a number of fields, it would be useful to count the number of drops of fluid released from a reservoir or source, or passing through a conduit. In some cases, it would also be useful to be able to determine and record the time period during which such drops are released. For example, in the medical field, ophthalmologists and other health professionals have long suspected that patients do not use their eyedrop medications as directed. It is therefore desirable to monitor the compliance of patients with directions for usage of eyedrops.

A number of attempts have been made to monitor patient compliance in ophthalmology. One such system used a base unit having a receptacle for a medication bottle. The (presumed) use of the medication is recorded by an electronic memory system, provided that the patient replaces the medication bottle into the base unit each time it is used. See R. Yee et al., Medication Monitor for Ophthalmology, *Amer. J. Ophthal.* 78:774–778 (1974). Disadvantages of this system are that the medication bottle can be easily separated from the base unit, the system is too bulky to fit conveniently in a pocket, and the appearance differs from commercially available bottles.

Further, this system does not monitor the amount of medication actually released from an eyedrop bottle, but only the approximate times that the bottle is removed from its receptacle.

A second system used a holding unit with a receptacle for a medication bottle. The (presumed) use of the medication is recorded by an electronic memory system when the bottle cap is removed. See S. Norell et al., A Medication Monitor and Fluorescein Technique Designed to Study Medication Behaviour, *Acta Ophthalmologica,* 58:459–467 (1980). Disadvantages of this system are that the system is too bulky to fit conveniently in a pocket and the appearance differs from commercially available bottles. Further, this system does not monitor the amount of medication actually released from an eyedrop bottle, but only the approximate times that the bottle cap is removed from the bottle.

A third system used a special bottle into which the contents of a medication bottle are transferred. The (presumed) use of the medication is recorded by an electronic memory system when the bottle cap is removed and the bottle is inverted. See Kass et al., A Miniature Compliance Monitor for Eyedrop Medication, *Arch Ophthalmol.,* 102:1550–1154 (1984). Disadvantages of this system are that the system requires transfer of medication from commercially available bottles, which may lead to contamination, and the system does not monitor the amount of medication actually released from an eyedrop bottle, but only the approximate times that the bottle cap is removed and the bottle inverted.

Ideally, an eyedrop compliance monitoring system would detect and record the actual number of eye drops used by a patient, and the time period during which the drops were used. This more accurate recorded information could then be read out by a doctor and used to evaluate the efficacy of a particular treatment.

Another advantage of being able to record both the number of drops released from a source and the time periods during which such drops are released is to provide a reminder signal or indication to a patient as to the dosage and appropriate time for each eyedrop administration.

Yet another advantage of being able to record both the number of drops released from a source and the time periods during which such drops are released is to monitor over and under medication by a patient. An alarm may be used in such a case to alert the patient of the condition.

It would be desirable to provide an eyedrop compliance monitoring system that may be adapted to these uses and which accommodates existing medication bottles, is inexpensive to manufacture, and is convenient to carry in a pocket or purse.

Accordingly, it is highly desirable to provide a compact, inexpensive, and accurate fluid drop counting and recording apparatus that optionally can "time stamp" the occurrence of drop releases and/or provide an indication as to the dosage and appropriate time for each eyedrop administration.

SUMMARY OF THE INVENTION

The present invention comprises a compact and inexpensive electronic apparatus which, in the preferred embodiment, is configured as a molded receptacle housing for receiving a commercially available eyedrop bottle in which the cap or the cap and nozzle has been replaced by the housing.

The inventive apparatus has a detection means that detects the separation of drops from a fluid supply bottle, and counts and records the number of such drops in a preset time period. Optionally, a real-time clock time stamps the stream of drop count data so that the absolute time period during which drops are released is also ascertained and recorded. Optionally, a reminder signal or indication is given to a patient as to the dosage and appropriate time for each eyedrop administration, or an alarm is given if drop dispensing is outside of a preset range (indicating over or under medication is occurring).

The preferred embodiment discloses a plastic receptacle housing suitable for receiving commercially available eyedrop bottles. The housing includes a nozzle which contains two or more electrically conducting probes. The probes, in conjunction with a high frequency oscillator, generate an electric field. Passage of a drop through this field and release of the drop from the fluid supply source generates a drop separation signal. An alternative embodiment is disclosed in which drop separation is detected optically. Each drop separation signal is detected by an analog detection and amplification circuit, thereby generating a drop "pulse" signal.

A digital circuit is provided which counts the number of drop pulses generated by the analog circuit, and stores the count (either as a binary number or as a bit-stream of binary signals) in a memory device. An internal clock is provided which is also coupled to the memory device. Control circuitry periodically stores a signal representative of a predetermined clock period in the memory device. A data communications interface is provided for coupling the drop counting apparatus to, for example, a microcomputer. The microcomputer system can download and analyze the recorded drop and time information in tabular, graphic, or other form. Such downloading of data may be made through a special adapter via direct electronic connection or fiber optic data link, or wireless transmission (e.g., radio frequency, infrared, or ultrasonic).

An alternative application is disclosed in which the drop detection and counting features of the invention are used in a feedback loop to control the rate of flow of fluid in a drop dispensing system.

Further aspects of the present invention will become apparent from the following detailed description when considered in conjunction with the accompanying drawings. It should be understood, however, that the detailed description and the specific examples, while representing the preferred embodiment and several alternative embodiments of the invention, are given by way of illustration only.

BRIEF DESCRIPTION OF THE DRAWINGS

FIG. 1 is a block diagram of the drop counting and recording system of the present invention.

FIG. 2 is a block diagram of the drop detection, counting and data storage circuitry of the present invention.

Like reference numbers in the various drawings refer to like elements.

DETAILED DESCRIPTION OF THE INVENTION

Figure 3:
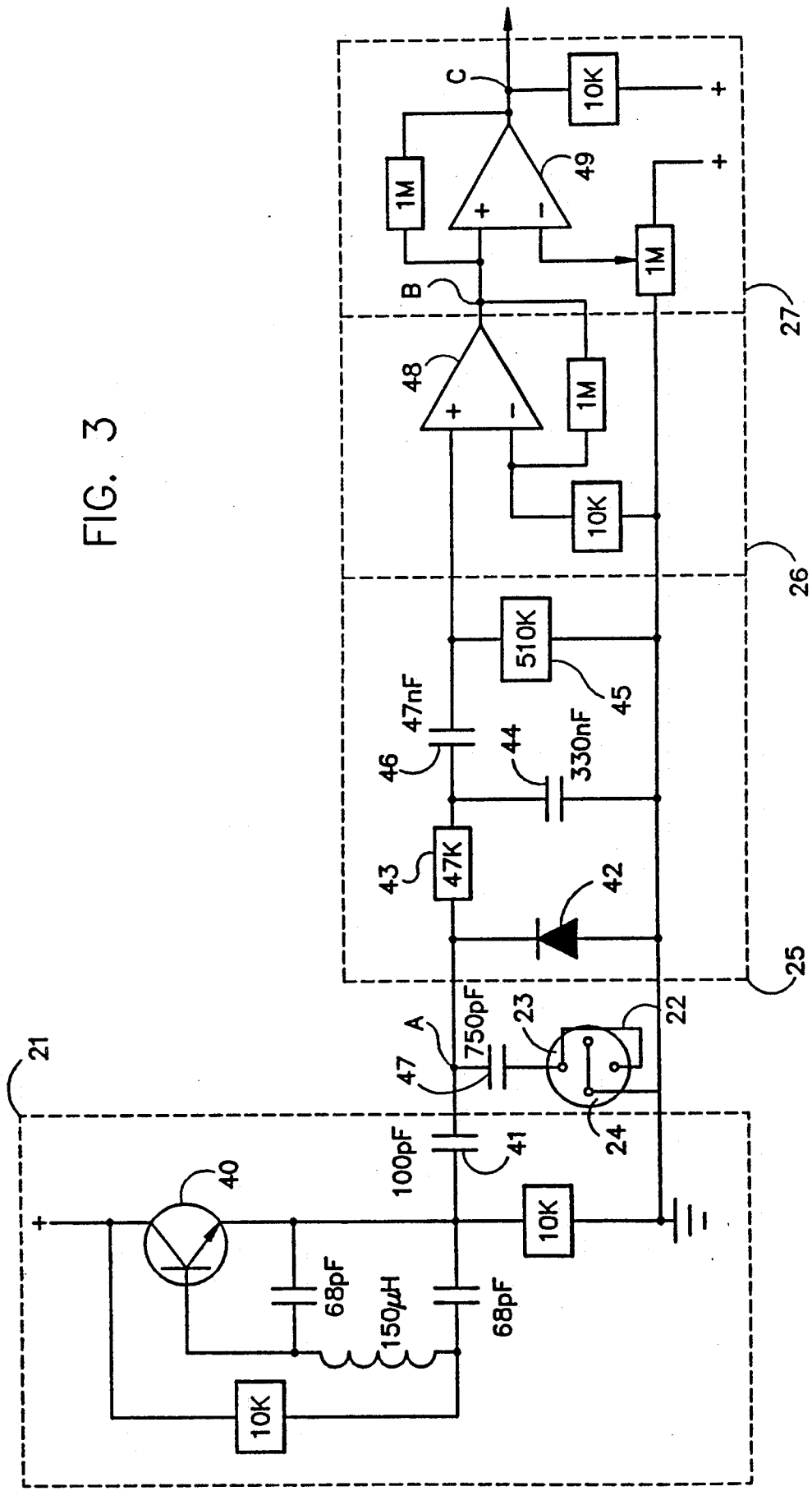
FIG. 3 is a detailed schematic diagram of the analog drop detection circuitry used in the preferred embodiment of the present invention for detecting drop separation (all resistance values are in ohms).

The following description is of the best presently contemplated modes of carrying out the invention. This description is made for the purpose of illustrating the general principles of the invention and should not be taken in a limiting sense.

In the preferred embodiment, the inventive drop counting apparatus uses a specialized nozzle that generates an electric field across the nozzle opening. When a drop passes through the electric field, detachment of the drop produces a distinctive disturbance in the electric field, which can be considered to be an electronic "separation signature" for the drop. In an alternative embodiment, the specialized nozzle detects separation of a drop by means of an optical detector. Upon detecting this separation signal, a digital pulse is generated and applied to a storage circuit to indicate the occurrence of a drop.

A real-time clock is also provided that periodically outputs a signal representative of the date and/or time, which signal is also stored in the memory unit to "time stamp" the occurrence of one or more drops. In the illustrated embodiment, the time stamping interval is recorded continuously, whether or not drops are detected. In an alternative embodiment, the time stamping of the occurrence of one or more drops is made on a "demand" basis, thereby conserving memory space.

In another embodiment, comparator and control circuitry is provided that compares the stored time and drop pulse data against preset or calculated values to determine if a patient has taken the proper amount of medication, and/or to signal the time and amount of medication that should be taken subsequently by the patient. If over or under medication has occurred (indicating drop dispensing is outside of a preset range), the control circuitry may provide an alarm signal to alert the patient and/or physician of such a condition.

FIG. 1 shows a block diagram of the basic inventive system. The invention comprises a nozzle sensor 10 which includes a physical nozzle through which fluid drops pass. A detection circuit 11 provides a means for generating a "signature" signal from the nozzle sensor 10 when a drop detaches from the nozzle. The signature signal is coupled to the detection circuit 11, which discriminates the separation of a drop from background noise and extraneous signals, resulting in a drop pulse. The drop pulse is coupled to a data storage circuit 12 which stores a signal representative of the number of drop pulses occurring in a specified time period, as well as a time stamp signal indicative of the beginning and end of the specified time period. The data storage circuit 12 can be coupled to an external device, such as a microcomputer, for retrieval and interpretation of the data stored in the data storage circuit 12.

FIG. 2 shows a block diagram of the basic circuitry used in the preferred embodiment of the inventive drop counting apparatus. An oscillator 21 generates a relatively high frequency AC bias voltage which is coupled to a specially constructed nozzle 22 attached to a supply of fluid (e.g., an eyedrop bottle). In the illustrated embodiment, the frequency of the bias voltage is about one megahertz. The nozzle 22 includes two electrodes 23, 24 spaced apart by dielectric material, the two electrodes 23, 24 thus comprising a capacitor. The high frequency AC bias voltage generated by the oscillator 21 creates an electric field between the electrodes 23, 24. The electrodes 23, 24 are situated with respect to the nozzle 22 such that a drop of fluid must pass through the electric field when squeezed out of the attached bottle.

A rectifying filter 25 is provided to convert the signal generated across the electric field into a positive voltage, to filter out any DC component of the signal, and to selectively pass only the drop "signature" portion of the signal waveform. The filtered signal passes through an amplifier 26 and then through a level discriminator 27, which ensures that the signal is greater than a predetermined level. The level discriminator 27 filters out noise and generates a square wave "drop pulse" signal suitable for use with digital circuitry.

The resulting drop pulse is then passed through a control circuit 30 whose output is connected to a memory device 31. The memory device 31 may be, for example, a random access memory used in conjunction with an addressing circuit to form a shift register. Other forms of memory devices can be used as desired, so long as the memory device is capable of storing a sequence of time-stamp signals and either distinct drop pulse signals (as in the illustrated embodiment), or a binary coded signal indicative of the number of drop pulses occurring in a particular time period.

A real-time clock circuit 32 periodically generates a signal indicative of the date and/or time. For example, the clock circuit 32 may generate a clock pulse every fifteen minutes on a continuous basis. The output of the clock circuit 32 is passed through the control circuit 30 such that the clock signal may be stored in the memory device 31 sequentially with the drop count data. In the illustrated embodiment, the clock circuit 32 outputs a periodic clock pulse. The stored periodic clock pulses thus designate preset periods which permit determination of the time period during which drops were released from the supply bottle.

Normally included is a data communications interface 33 for coupling the memory device 31 to external systems for reading out the time and drop count data. Such an interface may include a simple direct electronic connection or optical fiber data link, or may include circuitry for wireless transmission (e.g., radio frequency, infrared, or ultrasonic).

In the illustrated embodiment, the memory storage device 31 stores a sequence of values (for example, binary 1's) which indicate the occurrence of drop pulses, and periodically stores a value (for example, a binary "0") indicative of the occurrence of a clock pulse. Thus, a sequence of 0's may be stored in the memory storage device 31 if no drops are released from the bottle during a long interval (for example, several hours), and then a sequence of 1's may be stored in the memory device 31 between a preceding and succeeding binary 0, indicating that a number of drops, equal to the number of stored 1's, has occurred during the preset time period. If the memory device 31 is initialized at a known time, then the above-described sequence of binary 1's and 0's will indicate both the number of drops that have occurred in a particular time period, and the absolute time from the initialization point during which the drops occurred. This information can be read from an output of the memory device 31 and submitted to other computing circuitry (not shown), via the data communications interface 33, as data which can be graphically shown or displayed in a tabular or other format.

In an alternative embodiment, the clock circuit 32 outputs a binary number that represents an absolute time value. For example, the clock circuit 32 may output a 16-bit serial number. The first nine bits of the number represent a day of the year (or month and day), and the next 7 bits represent a 15-minute interval for each such day. Other coding schemes for designating the date and/or time could also be used. Such absolute time values are stored sequentially with the drop count data to time stamp either a sequence of drop count pulses or to time stamp a binary value representative of such a sequence. The number of stored drop pulse signals between stored time-stamp values, or the binary coded signal stored between time-stamp values which indicate the number of drop pulses occurring in a particular time period, indicate both the number of drops that have occurred in a particular time period, and the absolute time during which the drops occurred. Marker bits may be necessary to distinguish time values from drop count data and reduce the possibility of error. To further reduce the possibility of error, error correction coding may be added to each time-stamped drop count entry.

One advantage of such time stamping is that it does not depend on calculating actual dates and times in a relative manner when analyzing the stored drop count data, thus reducing the possibility of error.

Another advantage of such time stamping is that clock data need only be stored in the memory device if drop pulses have occurred during a preset period. For example, the control circuit 30 may include a counter that accumulates the number of drop pulses that occur in a fifteen minute interval (as determined from the clock circuit 32). If no drop pulses have occurred, then no data of any kind is stored in the memory device 31. If one or more drop pulses have occurred in the interval, then the current time stamp value from the clock circuit 32 is gated to and stored in the memory device 31, and the binary count (which may be limited to some number of bits, such as five or six) of the number of drops released in the interval is also gated to and stored in the memory device 31. Such "demand" time stamping thus saves memory space, since intervals in which no drops pulses have occurred are not time stamped.

FIG. 3 shows in greater detail the analog drop detection circuit used in the preferred embodiment of the inventive drop counting apparatus. The oscillator 21 and supporting circuitry comprises a transistor 40 coupled to passive feedback and biasing resistive, capacitive, and inductive elements as shown, such that the oscillator circuit 21 generates at its output a bias voltage modulated at approximately one megahertz. The bias voltage is applied across an AC coupling capacitor 41 coupled in series with the electrodes 23, 24 of the nozzle 22. The oscillator 21 may be implemented in a number of ways, including a crystal or an operational amplifier configured as an oscillator.

The rectifying filter 25 comprises a diode 42 and a number of passive resistive and capacitive elements coupled as shown in the preferred embodiment. Resistor 43 and capacitor 44 form an RC low-pass filter which blocks frequencies above about 100 KHz. Resistor 45 and capacitor 46 form an RC high-pass filter which blocks frequencies below about 50 Hz. The diode 42 rectifies the waveform passing through to the RC filters. A DC blocking capacitor 47 blocks any DC signal across the diode 42.

The output of the rectifying filter 25 is applied to the amplifier circuit 26, which comprises an operational amplifier 48 configured with feedback so as to amplify the input signal. The output of amplifier 26 is coupled to the level discriminator 27. The level discriminator comprises a second operational amplifier 49 configured and biased to pass only a signal having an amplitude greater than a predetermined level, thereby filtering out noise and generating a square wave signal suitable for use with digital circuitry.

Although an analog drop detection circuit has been disclosed in the illustrated embodiment, any circuit, digital or analog, that discriminates drop releases from other signals is suitable for use in the invention. For example, the analog drop detection circuit shown in FIG. 3 may be replaced by a sample-and-hold circuit coupled to an analog-to-digital converter. Digital signal processing techniques may then be used to detect drop detachments.

Figure 4:
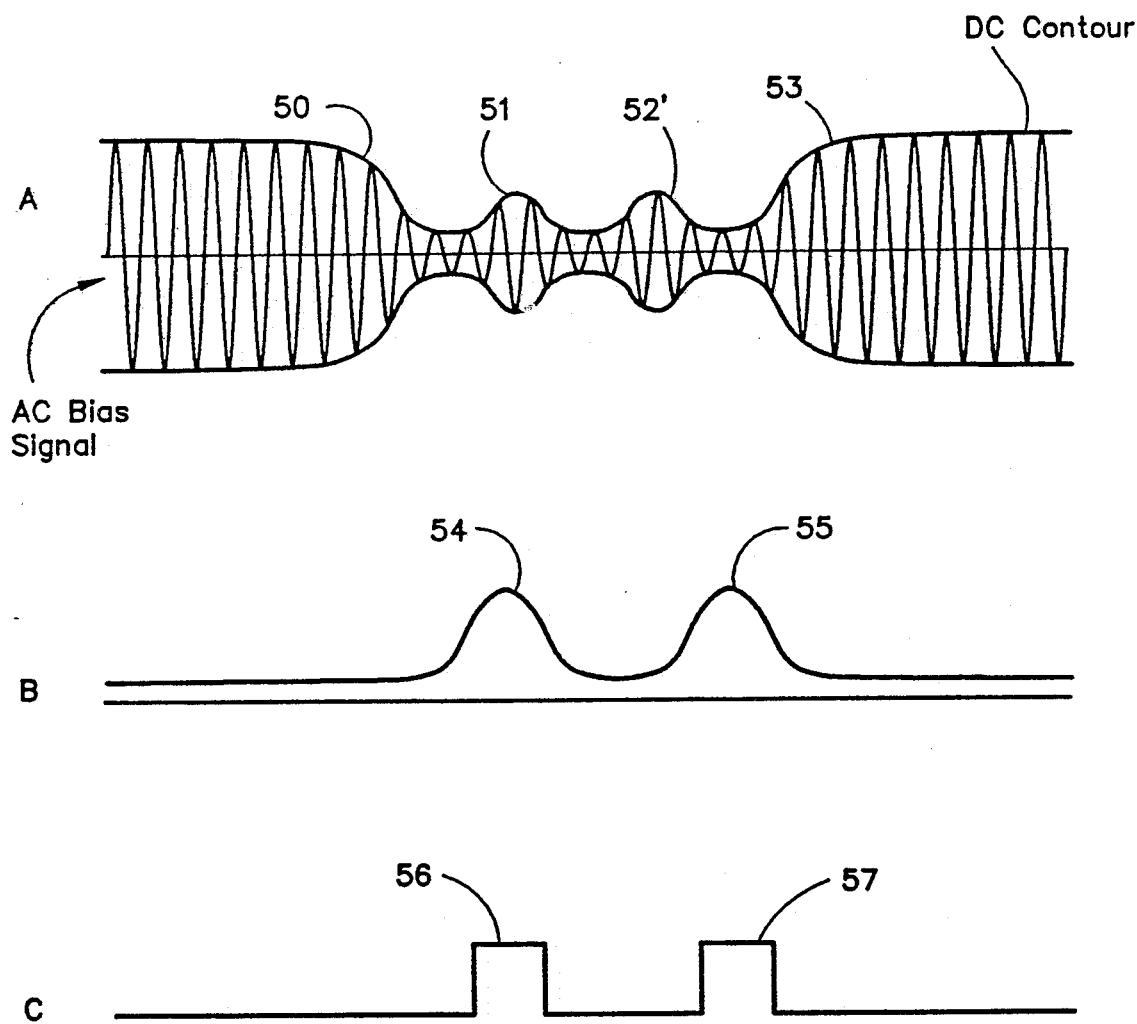
FIG. 4 is a diagrammatic sketch of the typical waveforms generated by the formation and release of a drop from a bottle of fluid, taken at points A, B, and C in FIG. 3.

FIG. 4 shows typical waveforms generated by the formation and release of a drop from a bottle of fluid, taken at points A, B, and C in FIG. 3. At point A, if no drop is being squeezed from the supply bottle, the waveform is a relatively constant amplitude one megahertz AC signal. The amplitude of the waveform decreases (as shown at region 50) as fluid begins to be squeezed through the nozzle 22 and changes the capacitance value of the nozzle sensor. When a drop detaches, the bulk of the fluid momentarily "rebounds" back through the tip of the nozzle 22, causing a distinct change in the waveform, as shown at region 51. A similar "separation signature" in the waveform occurs for each subsequent drop, as shown at region 52. As the bottle is released, the fluid pulls back from the nozzle 22, and the waveform returns to its quiescent state, as shown at region 53.

At point B, the waveform has been rectified, filtered, and amplified. If one or more drops have detached from the nozzle 22, the resulting signature signal appears at point B as shown at regions 54 and 55.

At point C, the waveform is held to binary values by the level discrimination circuit 27. If a drop is detected, the output at point C is a square wave drop pulse, as shown at regions 56 and 57.

Figure 5:
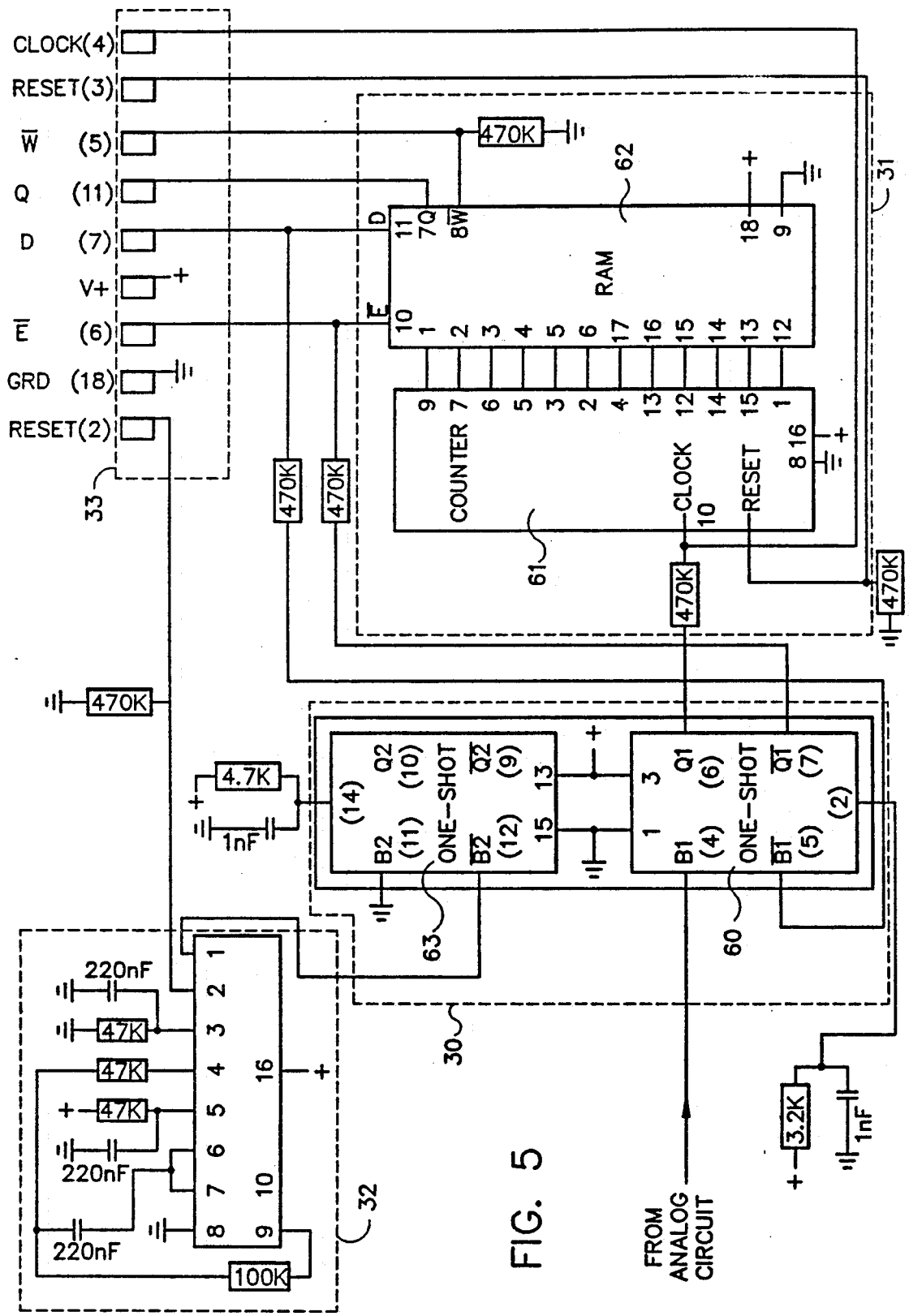
FIG. 5 is a detailed schematic diagram of the drop counting and data storage circuitry used in the preferred embodiment of the present invention (all resistance values are in ohms).
Figure 6:
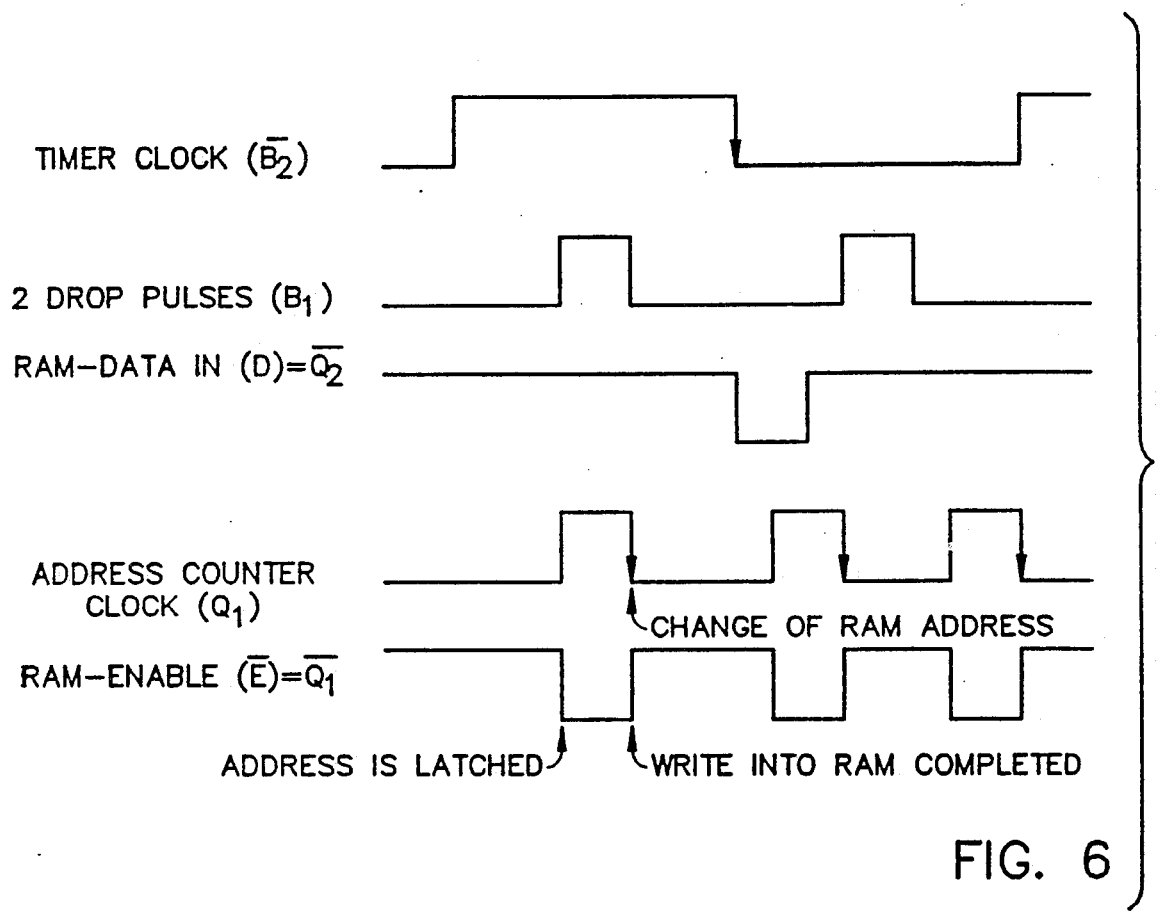
FIG. 6 is a timing diagram for the circuitry shown in FIG. 5.

The output of FIG. 3, which comprises drop pulses, is coupled to the digital drop counting and data storage circuitry shown in greater detail in FIG. 5. FIG. 6 shows a timing diagram for the circuitry shown in FIG. 5.

The input drop pulses are input to the B1 input of a first one-shot circuit 60, resulting in uniform-width opposite output pulses at outputs Q1 and $\overline{Q1}$. The output from Q1 is coupled to the CLOCK input of an incrementing counter circuit 61, the output of which is an address coupled to the address inputs of a random access memory (RAM) circuit 62.

The falling edge of Q1 causes the output of the counter 61 to change and thus increment to the next value.

The RAM 62 may comprise any addressable writable storage device, such as a dynamic RAM, a static RAM, an EEPROM, non-volatile RAM, or the like.

The output from $\overline{Q1}$ is coupled to the enable input $\overline{E}$ of the RAM 62. The address from the counter 61 is latched into the RAM 62 on the falling edge of $\overline{Q1}$. A write operation into the RAM 62 is complete on the rising edge of $\overline{Q1}$.

The output clock pulses of the clock circuit 32 are input to the $\overline{B2}$ input of a second one-shot circuit 63, resulting in a uniform-width output pulse at $\overline{Q2}$. $\overline{Q2}$ is coupled to data input D of the RAM 62, and to the $\overline{B1}$ input of the first one-shot 60.

The circuit shown in FIG. 5 thus generates a signal to the counter 61 and to the enable input $\overline{E}$ of the RAM 62 whenever (1) a drop pulse occurs, or (2) a clock pulse occurs. $\overline{Q2}$ is normally held high (i.e., a logical 1) if no clock pulse is present, and $\overline{Q2}$ comprises the data signal input to the RAM 62. Therefore, whenever a drop pulse occurs, a logical 1 is stored in the currently addressed storage location in the RAM 62, and then the address is sequentially incremented by the counter 61 to address a next storage location in the RAM 62. When a clock pulse occurs, $\overline{Q2}$ is forced low (i.e., a logical 0), and a logical 0 is stored in the currently addressed storage location in the RAM 62, and then the address is sequentially incremented by the counter 61 to address a next storage location in the RAM 62. (In order for the clock pulse signal to be properly recorded in the RAM 62, the width of the signal at $\overline{Q2}$ should be wider than the width of the $\overline{Q1}$ signal for the circuit shown).

Further circuitry may be added to that shown in FIG. 5 to disable further writing into the RAM 62 when it is full. Such circuitry may comprise, for example, a decoder configured to detect the highest address of the particular RAM integrated circuit used, coupled to an OR gate controlling the $\overline{Q1}$ input signal to the enable input $\overline{E}$ of the RAM 62.

Although a particular drop counting and data storage circuit has been disclosed in the illustrated embodiment, any circuit that counts and stores a representation of the number of drop pulses occurring in a preset time period, or which time stamps such representations, is suitable for use in the invention. For example, the combination of the counter 61 and RAM 62 may be replaced by a shift register or FIFO. The clock circuit 32 may be replaced by an RC oscillator, a crystal oscillator, or a counter coupled to the oscillator 21 used in the analog drop detection circuit shown in FIG. 3.

Figure 7:
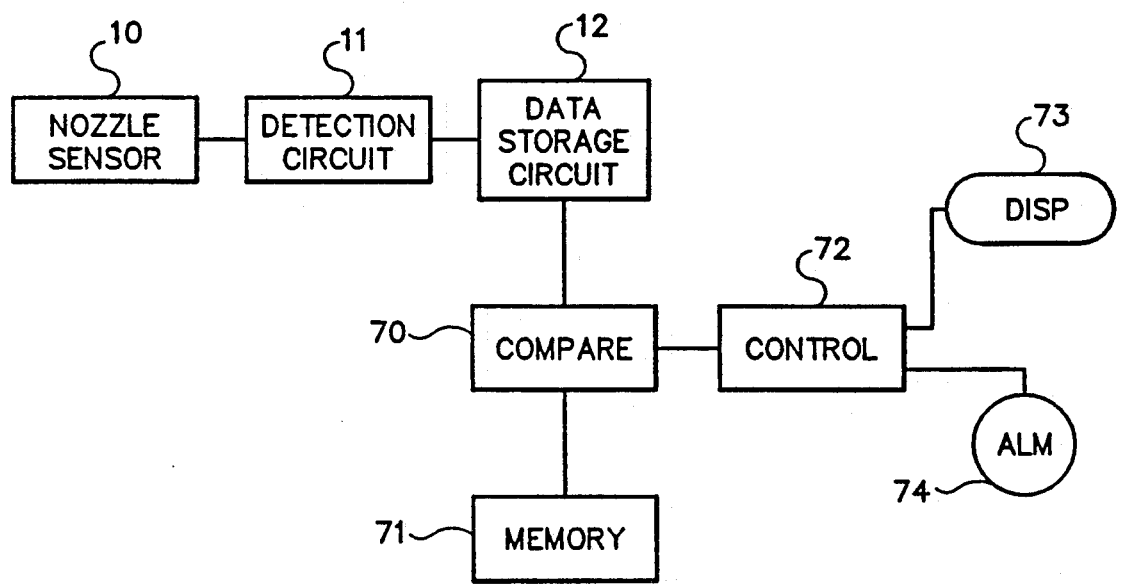
FIG. 7 is a block diagram of the drop counting and recording system of the present invention, further including dosage control and signaling circuitry.

FIG. 7 is a block diagram of the drop counting and recording system of the present invention, further including dosage control and signaling circuitry. Coupled to the data storage circuit 12 is a comparison circuit 70 that is also coupled to a dosage memory 71. Pre-loaded into the dosage memory 71 for each patient is data that includes the amount (or drop rate) and dosage release times (or ranges for such data) for optimal administration of medication. Additional data may be stored in the dosage memory 71, such as special administration instructions (e.g., the patient must avoid bright lights, or the medication is to be taken after a meal). A control circuit 72 (which may be, for example, a microprocessor or microcontroller circuit) is coupled to the comparison circuit 70.

As pulse data is accumulated and time stamped in the data storage circuit 12, the time and accumulated amount of each dosage is compared by the comparison circuit 70 to the preset values or value ranges. If a patient is over or under medicating, as indicated by the output of the comparison circuit 70, the control circuit 72 can so indicate to the patient on a display 73 (e.g., an LCD low power display) and/or by activating an alarm 74 (e.g., a piezoelectric buzzer). In addition or in the alternative, the control circuit 72 can store such occurrences in the data storage circuit 12 for later analysis by a physician.

In addition or in the alternative, the control circuit 72 may include a real-time clock. The comparison circuit 70 may compare the output of such a real-time clock to the preset times stored in the dosage memory 71. When the time occurs for medication administration, the control circuit 72 will so indicate to the patient on the display 73 and/or by activating the alarm 74. The amount of the dosage, or any special instructions, as preset in the dosage memory 71, may also be indicated on the display 73 to remind the patient.

Figure 8:
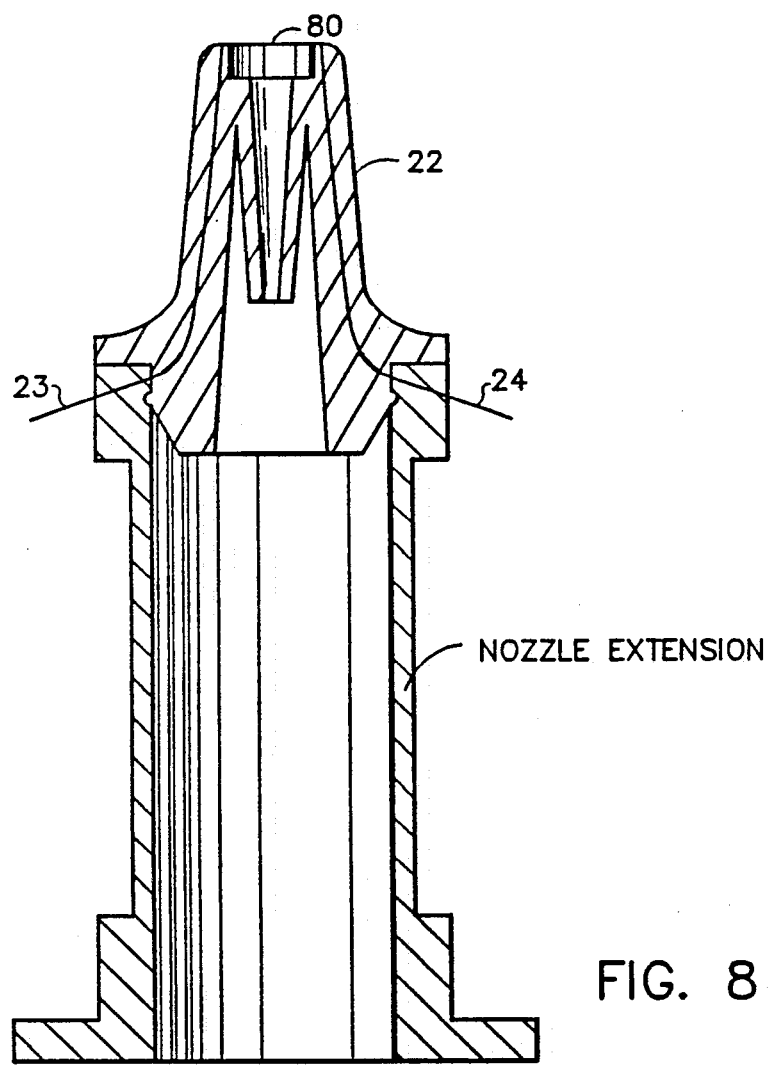
FIG. 8 is a cross-sectional view of a first embodiment of a nozzle tip sensor for use in conjunction with the present invention.

FIG. 8 shows a cross-sectional side view of the nozzle 22 of the presently preferred embodiment of the invention. Conductive electrodes 23 and 24 are provided which carry the AC bias voltage from the oscillator 21. The electrodes 23, 24 may be affixed to the surface of the nozzle 22, or embedded (as shown) within the plastic of the nozzle so that the electrodes do not come in contact with fluid passing through the nozzle opening 80. The electrodes 23, 24 may be of any conductive material, such as metal wire, conductive film, or metallic foil.

Figure 9:
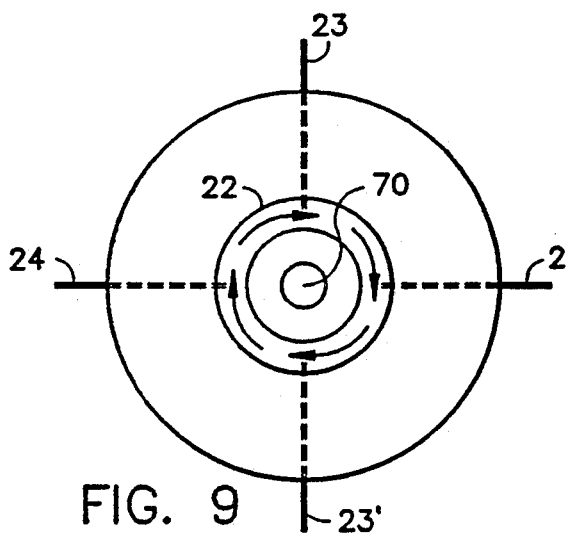
FIG. 9 is a top plan view of the nozzle tip sensor shown in FIG. 7.

Although two electrodes are shown in FIG. 8, in the preferred embodiment four electrodes 23, 23', 24, 24' (see top view of nozzle 22 in FIG. 9), in opposing pairs, are used in order to provide an electric field of relatively uniform cross section regardless of the orientation of a bottle using such a nozzle 22. More electrodes may be used if desired.

Figure 10:
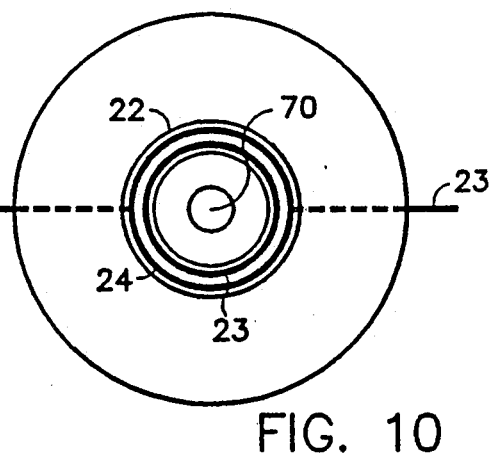
FIG. 10 is a top plan cross-sectional view of a second embodiment of a nozzle tip sensor for use in conjunction with the present invention.

FIG. 10 is a top plan side view of a second embodiment of a nozzle 22 for use in conjunction with the present invention. The electrodes 23, 24 comprise a pair of concentric rings forming the two plates of a capacitor.

Although particular configurations of electrodes 23, 24 have been disclosed in the illustrated embodiments, any configuration that serves to form a capacitive element such that detachment of a drop from the fluid supply causes a detectable change in the capacitance is suitable for use in the invention.

Figure 11:
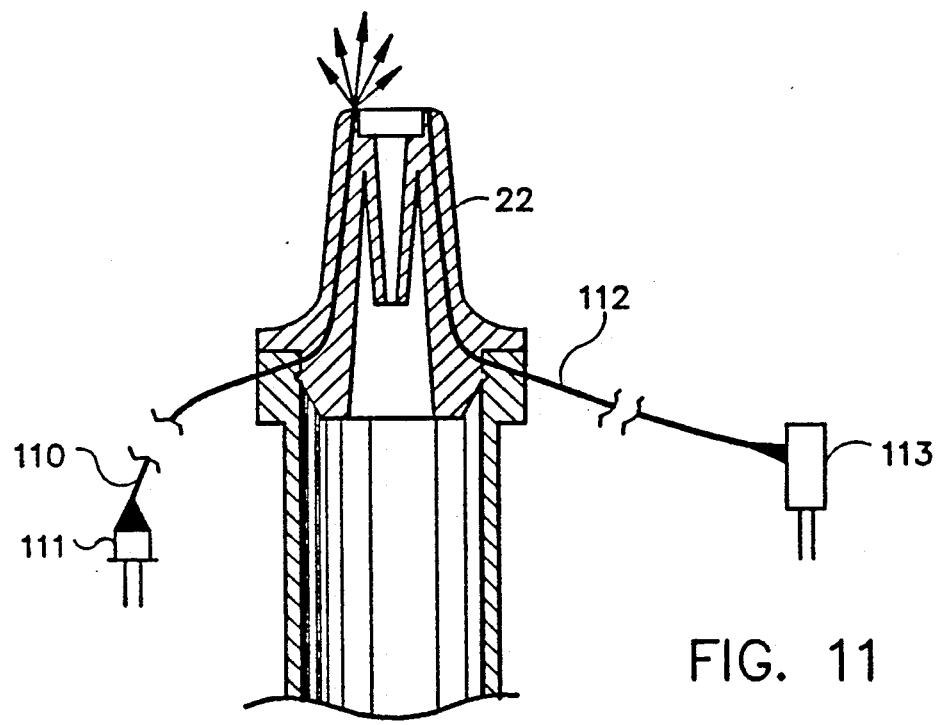
FIG. 11 is a cross-sectional view of a third embodiment of a nozzle tip sensor for use in conjunction with the present invention.

FIG. 11 is a cross-sectional view of a third embodiment of a nozzle tip sensor for use in conjunction with the present invention. Detection of drop separation is accomplished optically. A transmit optical guide 110 to coupled to a light source (such as an light emitting diode) 111. A receive optical guide 112 to coupled to a photodetector (such as a photodiode or phototransistor) 113. The transmit optical guide 110 and the receive optical guide 112 are situated in a nozzle 22 such that the light output of the transmit optical guide 110 is not directly aimed at the receive optical guide 112. However, the two optical guides are situated (for example, as shown in FIG. 11) such that internal reflection of light from the transmit optical guide 110 in a drop as the drop is being squeezed through the nozzle 22 is received in the receive optical guide 112. It has been found that as a drop detaches from the nozzle 22, a distinct "separation signal" is generated by the photodetector 113 that is similar to the separation signal generated by the capacitive nozzle tip sensor shown in FIG. 8.

Figure 12:
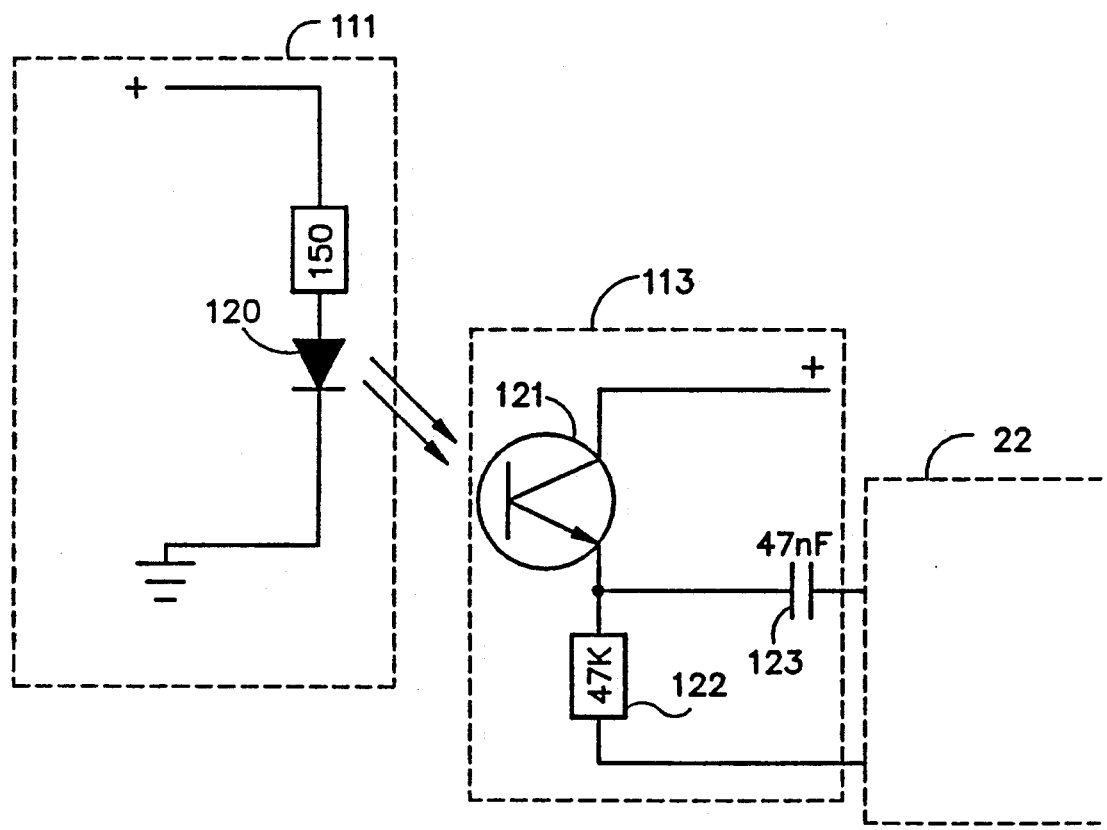
FIG. 12 is a schematic diagram of a portion of the drop detection circuitry used in conjunction with the nozzle tip sensor shown in FIG. 11.

FIG. 12 is a schematic diagram of a portion of the analog drop detection circuitry used in conjunction with the optical nozzle tip sensor shown in FIG. 11. An infrared LED 120 transmits light that is reflected to a phototransistor 121 when a drop is being output and released from the nozzle 22. The output current of the phototransistor 121 generates a voltage across a resistor 122. The voltage across the resistor 122 is coupled through a DC blocking capacitor to the rectifying circuit 22 (shown in detail in FIG. 3). The remainder of the detection circuit is as shown in FIG. 2. As noted previously, other detection circuitry, digital or analog, may be used to discriminate drop releases from other signals.

Figure 13:
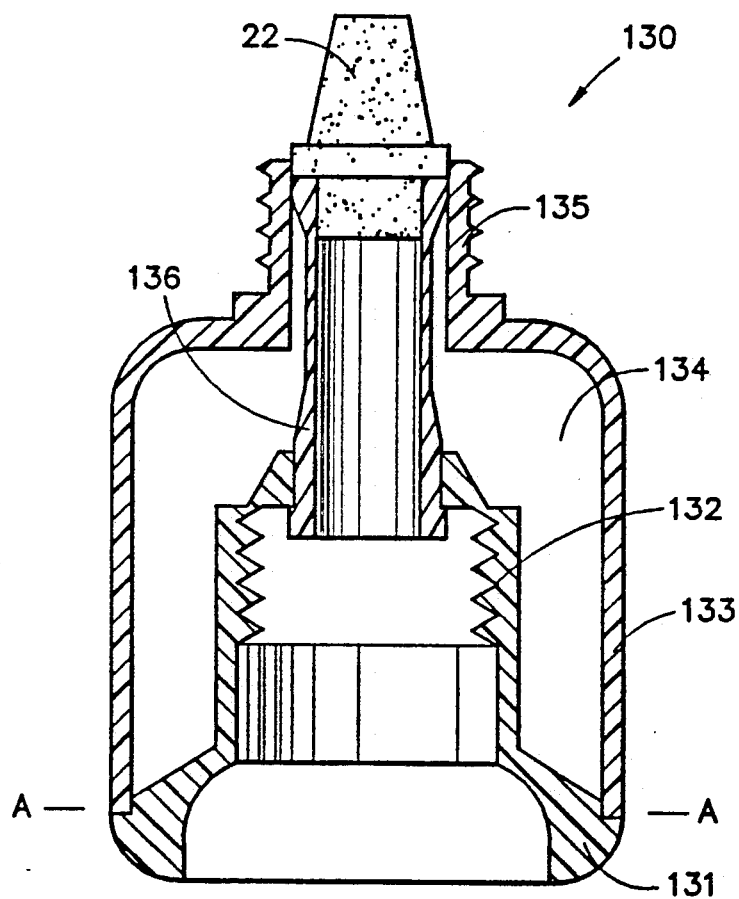
FIG. 13 is a cross-sectional view of the structure of the preferred embodiment of the present invention, showing a receptacle housing for receiving a bottle of fluid.

FIG. 13 is a cross-sectional view of the structure of the preferred embodiment of the present invention, showing a receptacle housing 130 for receiving a bottle of fluid. The housing 130 includes a receptacle shell 131 having an interior (or female) threaded neck 132 into which a correspondingly threaded standard fluid medication bottle can be screwed after removing its original cap, or cap and nozzle. An example of such bottles are the types used for eyedrops; such bottles typically come in 15 and 30 ml sizes. The interior threaded neck 132 may be molded integrally with the receptacle shell 131, or be a separate component attached to the receptacle shell 131.

Surrounding the receptacle shell 131 is an exterior shell 133 configured to create a circuit chamber 134 between the exterior shell 133 and the receptacle shell 131. The electronic circuitry described above is configured to fit within the circuit chamber 134 (for example, as surface mounted components on a flexible printed circuit board), along with batteries. Such batteries may be disposable or rechargeable. In the case of rechargeable batteries, it may be desirable to introduce electrical contacts through the exterior shell 133 to the batteries. The exterior shell 133 and receptacle shell 131 are preferably separable at a bottom juncture A so that the circuit chamber 134 can be accessed for repairs and/or to change batteries.

The top of the exterior shell 133 has an exterior (or male) threaded neck 135 for receiving a correspondingly threaded cap (not shown), which may be, for example, the original cap of the fluid medication bottle. The exterior threaded neck 135 may be molded integrally with the exterior shell 133, or be a separate component attached to the exterior shell 133.

Fitted within the exterior threaded neck 135 is a nozzle 22 of any of the types described above. The electrodes or signal connections of the nozzle 22 are coupled to the circuitry situated within the circuit chamber 134.

A connecting tube 136 couples the top of the inserted fluid medication bottle to the nozzle 22. The connecting tube 136 may be molded integrally with the interior threaded neck 132, or with the exterior shell 133 and/or exterior threaded neck 135. Alternatively, the connecting tube 136 may be a separate component coupled as shown in FIG. 13, or it can be part of the nozzle 22. In general, the length of the connecting tube 136 may vary depending on the dimensions selected for the components of the receptacle housing 130.

Power for all of the circuitry of the invention is provided by batteries (not shown). In order to preserve this limited power supply, the circuitry may include a switch that turns off power to all of the circuitry except the counter 61 and the RAM 62 (unless non-volatile RAM is used). Such a switch may comprise a microswitch that is closed upon opening the cap to the invention (this can be used in conjunction with a mercury switch that closes when the bottle is inverted), a membrane or pressure-sensitive switch around the bottle that is closed when the bottle is squeezed, a pressure sensitive switch within the bottle that closes when the bottle is squeezed, or any other switch providing a similar function. Further, if the storage device 31 is full, the remainder of the circuitry can be disabled or switched off to further conserve power.

Figure 14:
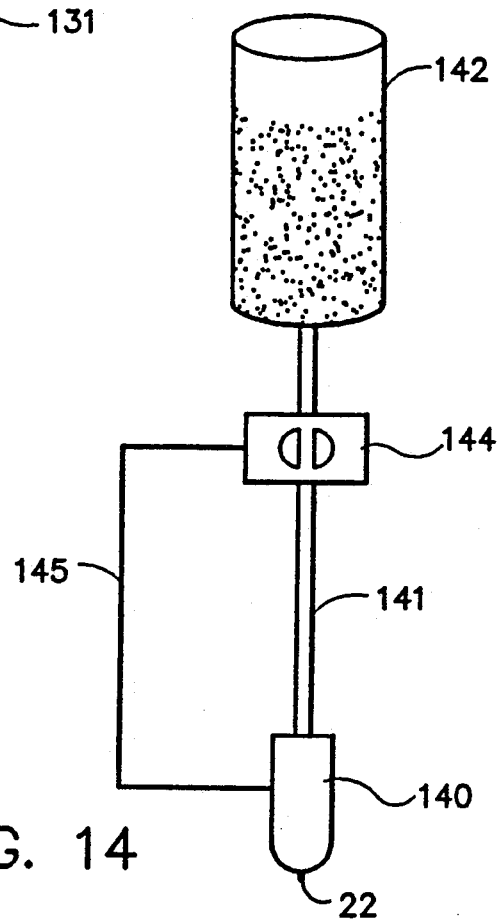
FIG. 14 is a diagrammatic view of the use of the invention in a feedback loop to control the flow of fluid in a drop dispensing system.

FIG. 14 is a diagrammatic view of another use of the invention in a feedback loop to control the flow of fluid in a drop dispensing system. A drop detecting and counting apparatus 140 in accordance with the present invention is coupled to the fluid output 141 of a fluid source 142. Interposed between the drop detecting and counting apparatus 140 and the fluid source 142 is a servo-controlled valve 144. The valve 144 is coupled via a control line 145 to the drop detecting and counting apparatus 140. Control circuitry in the drop detecting and counting apparatus 140 generates a valve control signal to regulate the opening and closing of the valve 144 in response to the rate of drop release from the nozzle 22 of the drop detecting and counting apparatus 140. By presetting a dosage memory (similar to that shown in FIG. 7) to the number of drops to be released in a particular time period, the control circuitry provides a feedback loop to the valve 144, regulating the release rate of fluid from the fluid source 142. Such an apparatus has use in intravenous medication administration and in laboratory environments where fluids are dispensed a drop at a time.

A number of embodiments of the present invention have been described. Nevertheless, it will be understood that various modifications may be made without departing from the spirit and scope of the invention. For example, rather than making a housing adapted to fit a standard eyedrop bottle, an integrated structure may be fabricated that combines into a single unit a fluid reservoir and the detection, counting, and recording apparatus of the present invention. Further, other tip sensors can be used to detect separation of drops, such as an inductive coil through which the drops pass, or magnetic sensors if the fluid has magnetic properties. Accordingly, it is to be understood that the invention is not to be limited by the specific illustrated embodiment, but only by the scope of the appended claims.

We claim:

1. An electronic drop counting device, including:
   a. sensor means, coupled to a source of fluid, for generating a distinctive signal upon the separation of a drop of fluid as it separates from the source of fluid;
   b. detection means, coupled to the sensor means, for receiving the output of the sensor means, detecting each distinctive signal, and generating a drop pulse in response to such detection.

2. The electronic counting device of claim 1, further including counting means, coupled to the detection means, for generating a count signal indicative of the number of drop pulses received from the detection means.

3. The electronic counting device of claim 2, further including recording means, coupled to the counting means, for receiving and storing each count signal.

4. The electronic counting device of claim 3, further including data communications interface means, coupled to the recording means, for transmitting the stored count signals as binary-encoded data to an external electronic device.

5. The electronic counting device of claim 3, further including clock means, coupled to the recording means, for generating a time signal indicative of a preset time period, and wherein the recording means includes means for storing each time signal to indicate the number of count signals received by the recording means during each such preset time period.

6. The electronic counting device of claim 3, further including clock means, coupled to the counting means, for generating a time signal indicative of the time each count signal is received, and wherein the recording means includes means for storing each time signal.

7. The electronic counting device of claim 3, further including clock means, coupled to the counting means, for generating a time signal indicative of the time each non-zero count signal is received, and wherein the recording means includes means for storing each time signal.

8. The electronic counting devices of claims 5, 6, or 7, further including:
   a. memory means for storing drop quantity and release time data;
   b. comparison means, coupled to the memory means and the recording means, for comparing recorded count signals and time signals against the stored drop quantity and release time data, and generating a comparison signal indicative of the result of such comparison;
   c. control and signaling means, coupled to the comparison means, for generating a drop dispensing reminder signal in response to the comparison signal.

9. The electronic counting device of claim 8, wherein the control and signaling means further includes means for indicating that the recorded count signals and time signals are outside of a preset range of stored drop quantity and release time data.

10. The electronic counting device of claim 5, wherein each count signal is stored by the recording means as a first binary value, and each time signal is stored by the recording means as a second binary value.

11. The electronic counting device of claim 2, further including:
   a. controllable valve means, coupled to the source of fluid, for regulating the flow of fluid from the source of fluid;
   b. control means, coupled to the controllable valve means and to the counting means, for generating and transmitting control signals to the valve means in response to the count signals received from the counting means, to thereby regulate the rate of flow of fluid from the source of fluid.

12. The electronic counting device of claim 1, wherein the sensor means includes a capacitive sensor.

13. The electronic counting device of claim 12, wherein the capacitive sensor includes oscillator means, coupled to the capacitive sensor, for generating an alternating electrical field across the capacitive sensor, wherein the separation of a drop of fluid through the sensor field generates said distinctive signal.

14. The electronic counting device of claim 1, wherein the sensor means includes an optical sensor.

15. The electronic counting device of claim 14, wherein the optical sensor includes:
   a. light source means for illuminating the fluid drops;
   b. photodetector means for receiving reflected light indicative of the separation of a drop of fluid through the sensor, and for generating said distinctive signal in response to such separation.

16. The electronic counting device of claim 1, wherein the detection means includes:
   a. filter means, coupled to the sensor means, for distinguishing each distinctive signal received from the sensor means from extraneous signals;

b. amplification means, coupled to the filter means, for amplifying each filtered distinctive signal;

c. level discrimination means, coupled to the amplification means, for generating a drop pulse from each filtered distinctive signal.

17. A method of counting drops using an electronic drop counting device, including the steps of:

a. sensing the release of a drop of fluid as it seperates from a source of fluid and generating a distinctive signal thereupon;

b. detecting each distinctive signal and generating a drop pulse in response to such detection;

c. generating a count rate signal indicative of the number of drop pulses occurring in a preset time period;

d. storing each count rate signal in a memory device.

18. The method of counting drops using an electronic counting device of claim 17, further including the step of transmitting the stored count rate signals to an external device.

19. An electronic drop counting device, including:

a. sensor means, coupled to a source of fluid, for generating a distinctive signal upon detection of a drop of fluid as it separates from the source of fluid;

b. detection means, coupled to the sensor means, for receiving the output of the sensor means, detecting each distinctive signal, and generating a drop pulse in response to such detection;

c. counting means, coupled to the detection means, for generating a count signal indicative of the number of drop pulses received from the detection means;

d. clock means for generating a time signal indicative of a present time period;

e. recording means, coupled to the counting means and the clock means, for receiving and storing each count signal, and for receiving and storing each time signal to indicate the number of count signals received by the recording means during each such preset time period.

20. An electronic drop counting device, including:

a. sensor means, coupled to a source of fluid, for generating a distinctive signal upon detection of a drop of fluid as it separates from the source of fluid;

b. detection means, coupled to the sensor means, for receiving the output of the sensor means, detecting each distinctive signal, and generating a drop pulse in response to such detection;

c. counting means, coupled to the detection means, for generating a count signal indicative of the number of drop pulses received from the detection means;

d. clock means for generating a time signal indicative of the time each count signal is received;

e. recording means, coupled to the counting means and the clock means, for receiving and storing each count signal and each time signal.

21. The electronic counting device of claim 20, wherein the time signal is generated only for each non-zero count signal.

22. The electronic counting device of claims 19 or 20, further including data communications interface means, coupled to the recording means, for transmitting the stored count signals as binary-encoded data to an external electronic device.

23. The electronic counting device of claims 19 or 20, further including:

a. memory means for storing drop quantity and release time data;

b. comparison means, coupled to the memory means and the recording means, for comparing recorded count signals and time signals against the stored drop quantity and release time data, and generating a comparison signal indicative of the result of such comparison;

c. control and signaling means, coupled to the comparison means, for generating a drop dispensing reminder signal in response to the comparison signal.

24. The electronic counting device of claim 23, wherein the control and signaling means further includes means for indicating that the recorded count signals and time signals are outside of a preset range of stored drop quantity and release time data.

25. The electronic counting device of claims 19 or 20, wherein the detection means includes:

a. filter means, coupled to the sensor means, for distinguishing each distinctive signal received from the sensor means from extraneous signals;

b. amplification means, coupled to the filter means, for amplifying each filtered distinctive signal;

c. level discrimination means, coupled to the amplification means, for generating a drop pulse from each filtered distinctive signal.

26. The electronic counting device of claim 1, 19 or 20, further including display means for displaying count-related information.

* * * * *